(12) United States Patent
Wang et al.

(10) Patent No.: US 10,335,398 B2
(45) Date of Patent: Jul. 2, 2019

(54) BIOADHESIVE COMPOSITIONS FOR INTRANASAL ADMINISTRATION OF GRANISETRON

(71) Applicant: MAXINASE LIFE SCIENCES LIMITED, Hong Kong (CN)

(72) Inventors: Yanfeng Wang, Hong Kong (CN); Benjamin Tak Kwong Lee, Hong Kong (CN); Johnson Yiu Nam Lau, Newport Beach, CA (US)

(73) Assignee: MAXINASE LIFE SCIENCES LIMITED, Hong Kong (CN)

(*) Notice: Subject to any disclaimer, the term of this patent is extended or adjusted under 35 U.S.C. 154(b) by 0 days.

(21) Appl. No.: 15/564,824

(22) PCT Filed: Apr. 8, 2015

(86) PCT No.: PCT/CN2015/000248
§ 371 (c)(1),
(2) Date: Oct. 6, 2017

(87) PCT Pub. No.: WO2016/161537
PCT Pub. Date: Oct. 13, 2016

(65) Prior Publication Data
US 2018/0117019 A1    May 3, 2018

(51) Int. Cl.
| | | |
|---|---|---|
| *A61K 9/00* | (2006.01) | |
| *A61K 9/06* | (2006.01) | |
| *A61P 1/08* | (2006.01) | |
| *A61K 47/02* | (2006.01) | |
| *A61K 47/10* | (2017.01) | |
| *A61K 47/18* | (2017.01) | |
| *A61K 47/32* | (2006.01) | |
| *A61K 47/34* | (2017.01) | |
| *A61K 47/36* | (2006.01) | |
| *A61K 47/38* | (2006.01) | |
| *A61K 47/42* | (2017.01) | |
| *A61K 31/439* | (2006.01) | |

(52) U.S. Cl.
CPC .......... *A61K 31/439* (2013.01); *A61K 9/0043* (2013.01); *A61K 9/06* (2013.01); *A61K 47/02* (2013.01); *A61K 47/10* (2013.01); *A61K 47/186* (2013.01); *A61K 47/32* (2013.01); *A61K 47/34* (2013.01); *A61K 47/36* (2013.01); *A61K 47/38* (2013.01); *A61K 47/42* (2013.01); *A61P 1/08* (2018.01)

(58) Field of Classification Search
None
See application file for complete search history.

(56) References Cited

U.S. PATENT DOCUMENTS

| 7,947,257 B2 | 5/2011 | Watts et al. |
| 2009/0047234 A1 | 2/2009 | Touitou et al. |
| 2009/0275668 A1 | 11/2009 | Kamishita |

FOREIGN PATENT DOCUMENTS

| CN | 101296686 | 10/2008 |
| EP | 3078367 A | 10/2016 |
| TW | 201639566 A | 11/2016 |
| WO | 2007043057 A2 | 4/2007 |

OTHER PUBLICATIONS

International Search Report and Written Opinion dated Jan. 14, 2016 in PCT Application No. PCT/CN2015/000248.
Office Action dated Aug. 3, 2017 in European Patent Application No. 16162215.4.
Office Action dated Feb. 23, 2018 in European Patent Application No. 16162215.4.
Ahmed, Sami, et al. "Provesicular granisetron hydrochloride buccal formulations: In vitro evaluation and preliminary investigation of in vivo performance," European Journal of Pharmaceutical Sciences, vol. 60, pages 10-23, Aug. 2014.
Xingmei, Wu. "Preparation of Granisetron Hydrochloride Nasal Thermosensible Gels and Its Release Behavior In vitro" Abstract Only, Chemical Abstracts Service, Database accession No. 2008:1179562. Retrieved from URL: http://en.cnki.com.cn/Article_en/CJFDTOTAL-YYGZ200816042.htm on Jun. 25, 2018, Zhongguo Yaoye (2008), 17(16), pp. 49-50 (abstract).

*Primary Examiner* — Brian J Davis
(74) *Attorney, Agent, or Firm* — McDermott Will & Emery LLP

(57) ABSTRACT

Sprayable aqueous pharmaceutical compositions containing granisetron or a pharmaceutically salt thereof, and pharmaceutically acceptable inactive ingredients, including tonicity agents, preservatives, and water soluble polymers with bioadhesive properties and/or capable of changing the rheological behavior in relation to ions, pH and temperature. The compositions are intranasally administered to a subject in need thereof in the rapid management and or prevention of nausea and/or vomiting induced by cytotoxic chemotherapy, radiation, or surgery. The composition has the advantages of rapid absorption and onset of action, prolonged drug plasma concentration and pharmacological effects comparable to intravenous infusion, as well as reduced nasal stinging sensation.

21 Claims, 7 Drawing Sheets

BIOADHESIVE COMPOSITIONS FOR INTRANASAL ADMINISTRATION OF GRANISETRON

TECHNICAL FIELD

This invention relates to a pharmaceutical composition, particularly a bioadhesive composition comprising granisetron or a pharmaceutically salt thereof, as the active ingredient for intranasal administration with enhanced and prolonged granisetron absorption as well as reduced nasal stinging and dripping. The composition is suitable for rapid and sustained prevention and/or relief of nausea and/or vomiting induced by cytotoxic chemotherapy, radiation, or surgery.

BACKGROUND ART

Nausea and vomiting are commonly and severely debilitating adverse events of cytotoxic chemotherapy, radiotherapy, and certain types of surgeries. These symptoms limit patients' ability to eat and drink, remarkably reduce quality of life, threat the success of therapy (Sussman N, Anticancer Drugs 1995; 6(suppl 1):4-8). It has been reported that up to 20% of patients were forced to postpone or refuse potentially curative treatment (Herrstedt J, Support Care Cancer 2002; 10:85-87). The management of chemotherapy-induced, radiotherapy-induced, and postoperative nausea and vomiting (CINV, RINV, and PONV) has improved greatly recently with the introduction of 5-HT3-receptor-antagonists (5-HT3-RAs) (Jordan K et al., Critical Reviews in Oncology/Hematology 2007; 61:162-175). The 5-HT3-RAs, also known as "setrons", are widely regarded as the most efficacious antiemetics available today and currently recommended as the first choice to control CINV, RINV and PONV (Annual Oncology 1998; 9:811-819).

Granisetron (1-methyl-N-((1R,3r,5S)-9-methyl-9-azabicyclo[3.3.1]nonan-3-yl)-1H-indazole-3-carboxamide; CAS No.: 109889-09-0) is a potent and highly selective 5-HT3-RA, it is effective and well-tolerated for preventing CINV, RINV and PONV (de Genolier C G, The Oncologist 2004; 9:673-686).

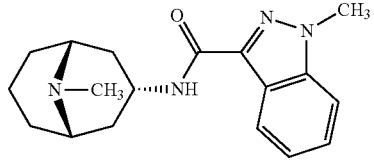 [SMILES: CN1[C@@H]2CCC[C@H]1C[C@@H](NC(=O)c1nn(C)c3ccccc13)C2]

The available dosage forms of granisetron in the market include oral tablet/solution (Kytril®), transdermal patch (Sancuso®), and intravenous injection (Kytril®). The onset of oral tablet or transdermal patch, however, is relatively slow (at least 1 hour for PO route and 24 hrs for transdermal route), and oral dosing of the tablets may be extremely difficult when patients are suffering from nausea and vomiting and the swallowing capacity is compromised. Granisetron IV injection can achieve rapid pharmacological effect (5 minutes), however, it is invasive and patients will suffer unnecessary pains and potential side-effects related to the injection, not to mention the extra staff time and procedure involved in administer the injectable medication. Therefore, it is imperative to seek an alternative dosage form that is ease of use, non-invasive, safe with rapid onset for better manage.

In light of the aforementioned limitations of oral, transdermal and injectable granisetron products, there is a need for an alternative route of administration, for example, there being interests shown in intranasal administration. Intranasally absorbed melatonin will directly enter into systemic circulation, and the first-pass hepatic metabolism is completely avoided (Bechgaard E et al., Int J Pharm 1999; 182:1-5). Meanwhile, the nasal mucosa has less proteolytic activity than the gastrointestinal tract (Zhou X H and Po L W, Int J Pharm 1990; 68:241-250), thus both rapid pharmacological onset and high bioavailability are expected to achieve after intranasal administration. Intranasal delivery is also ease-of-use, safe, and allow patient self-dose as needed. Granisetron is a small and lipophilic molecule with acceptable water solubility and stability; compared to other setron drugs (i.e. ondansetron), the dose of granisetron is low (1-2 mg/person/day), therefore, it is a possible candidate for intranasal delivery. However, up till now, nobody was able to come up with an effective formulation that works for intranasal delivery.

Due to nasal mucociliary clearance, substances administered intranasally are rapidly removed from the nasal cavity, with the mean clearance half-life of approximately 21 min (Soane R J et al., Int J Pharm 1999; 178: 55-65). MCC may result in short nasal residence time, limited drug absorption and insufficient pharmacologic effect (Ugwoke M I et al., J Pharm Pharmacol, 2001; 53, 3-22).

Intranasal composition comprising granisetron was firstly disclosed in CN patent no. ZL021176716.8. Granisetron hydrochloride, together with preservatives and tonicity agents, were dissolved in water and then filtrated and filled into spray device. After intranasal administration of the solution formulation in beagle dogs, the drug plasma concentration ($C_{max}$) increased 1.5-5 fold as compared to that after administration of oral tablets. The time to reach $C_{max}$ ($T_{max}$) was reduced from 1.5 hr (oral) to 0.31 hr (intranasal). However, the relatively bioavailability (intranasal to oral) was only 111.88%, indicating that drug solution was rapidly removed by nasal mucociliary clearance (MCC) after intranasal administration, resulting in low systemic exposure (AUC) despite of much higher $C_{max}$.

The mucoadhesive technology utilizes the bioadhesive properties of certain water-soluble polymers, which become adhesive on hydration, and hence can be used for targeting a drug to a particular region of the body (i.e. epithelial tissue) for extended periods of time (Asane G S et al., Drug Del Ind Pharm, 2008; 34, 1246-1266).

U.S. Pat. No. 7,947,257, incorporated herein by reference, disclosed the compositions containing chitosan (a salt or derivative) for intranasal administration of granisetron or the pharmaceutically salts. Chitosan is a cationic polymer with bioadhesive properties, has been shown to improve the systemic bioavailability of granisetron after intranasal administration in sheep, with shorter time to maximum plasma concentration ($T_{max}$). This composition, unfortunately, cause nasal irritation and painful sensation and is not suitable for human use.

U.S. Pat. No. 8,827,946, incorporated herein by reference, and descripted a dry powder granisetron composition for intranasal delivery. To deliver accurate and sufficient amount of powder into nasal cavity, a complicated and costly spray device by compressed air was utilized. The spray dose uniformity and reproducibility, unfortunately, are poor, with high risk of inhalation into lung. The physicochemical stability of dry powder is more susceptible to the environmental humidity. Furthermore, nasal irritation induced by the high local drug concentration where the drug powder accumulates is a common issue after intranasal delivery of powder formulations.

In view of the issues existed in the prior art, there is a clear need for a new and special composition with controlled and prolonged drug release when sprayed onto nasal mucosa, reduced the stinging sensation, improved and sustained anti-vomiting/nausea effects.

SUMMARY OF INVENTION

One object of the present invention is to provide a sprayable aqueous composition, which comprises granisetron or a pharmaceutically salt thereof, and pharmaceutically acceptable inactive ingredients, including water soluble polymers with bioadhesive properties and/or capable of changing the rheological behavior in relation to ion, pH and temperature, and optionally tonicity agents and preservatives. Granisetron or a pharmaceutically salt thereof in the composition can be rapidly and completely absorbed from nasal mucosa after administration. The compositions are suitable for intranasally administered to a subject in need thereof in the prevention or relief of nausea and vomiting induced by cytotoxic chemotherapy, radiation, or surgery, with the advantages of rapid and prolonged absorption, as well as reduced nasal stinging sensation.

Another object of the present invention is to provide a pharmaceutical composition, comprising (a) granisetron or a pharmaceutically salt, (b) at least one aqueous vehicle polymer that is selected from a group consisting of rheology-changeable polymer, bioadhesive polymer and the combination thereof.

In some embodiments of the invention, the rheology-changeable polymer is selected from a group consisting of pH-Sensitive polymer, Temperature-Sensitive polymer, Ion-sensitive polymer and the combinations thereof. Said pH-Sensitive polymer is capable of changing the rheological behavior in relation to pH change when the drug solution is mixed with nasal fluid. Said Temperature-Sensitive polymer is capable of changing the rheological behavior in relation to temperature change when sprayed into nasal cavity. Said Ion-sensitive polymer is capable of changing the rheological behavior in presence of ions in nasal fluid.

In some embodiments of the invention, the rheology-changeable polymer is selected from a group consisting of carbomer, carrageenan, cellulose acetate phthalate, gellan gum, pectin, sodium alginate, poloxamer, and the combinations thereof.

According to one aspect of the present invention, aqueous vehicle polymers are with bioadhesive properties and/or capable of changing the rheological behavior in relation to ion, pH and temperature, respectively. Such compositions can keep low viscosity when the drug solution is stored in the container, allowing easily spraying into nasal cavity. The viscosity of the solution will then dramatically increase, for instances, by ions in nasal fluids, pH or temperature changes in nasal cavity, resulting in a viscous gel which ensures a better and longer contact with the nasal mucosa as well the reduced nasal stinging sensation by slow release of active ingredient to nasal mucosa. To our surprise, the inventors found that after intranasal administration of the bioadhesive compositions in mammals, an early and high plasma concentration of the active ingredient can be generated, which is comparable to or higher than that after intravenous infusion, the high plasma concentration can be lasted for at least 3 hours. This profile in highly unusual and exceeds our initial expectations.

According to another aspect of the present invention, the compositions deliver 0.1 to 20 mg granisetron or a pharmaceutically salt thereof after intranasal administration, with a spray dosage ranging from 10 to 200 µL in each nostril. Again, the ability to deliver an effective clinical dose with such a surprisingly low intranasal administration make this invention into a feasible clinical utility.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DESCRIPTION OF EMBODIMENTS

Figure 1:
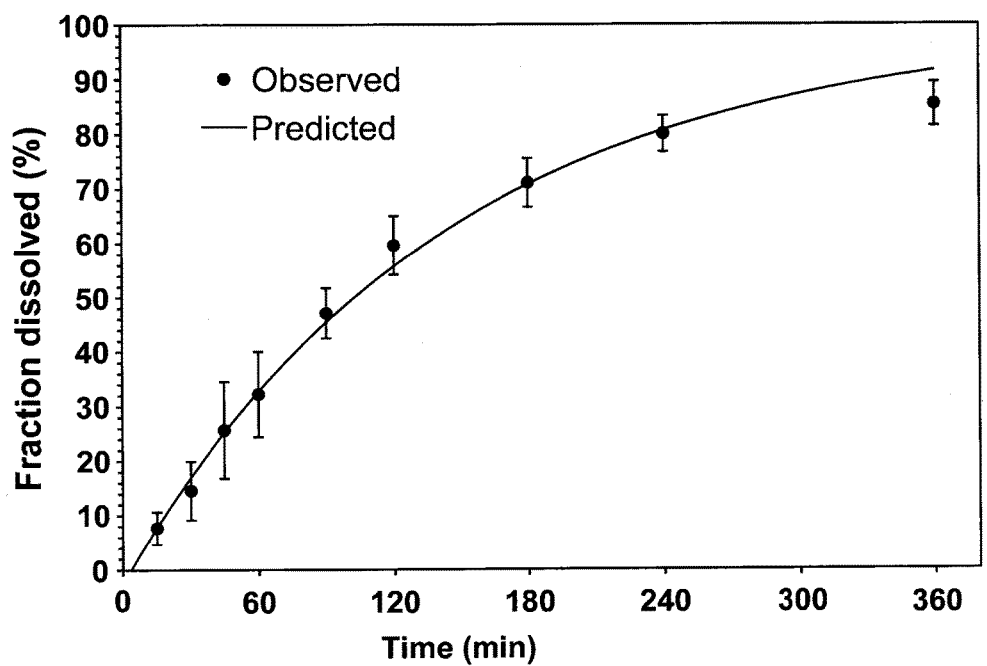
FIG. 1 shows granisetron hydrochloride release profile from gellan gum based ion-sensitive composition.

Embodiments of the present invention provide a novel method of intranasal delivery of compositions containing granisetron or a pharmaceutically salt thereof. In comparison to the conventional granisetron intravenous infusion and tablets, intranasal compositions can offer several advantages such as non-invasive, easy to use without water, self-dose, rapid absorption and fast onset, high bioavailability, prolonged pharmacological effects, and reduced nasal stinging sensation, such compositions are therefore especially suitable for rapid and sustained prevention or relief of nausea and vomiting induced by cytotoxic chemotherapy, radiation, or surgery.

The composition according to the present invention includes the active ingredient, i.e., granisetron or a pharmaceutically salt thereof. Granisetron used in current invention includes both in the form of free base or the pharmaceutically acceptable salts. The pharmaceutically acceptable salts include, but not limited to acetate, benzenesulfonate, benzoate, bicarbonate, bromide, calcium edentate, camsylate, carbonate, citrate, edatate, edisylate, estolate, esylate, fumarate, gluceptate, gluconate, glutamate, glycollylarsinate, hexylresorcinate, hydrabamine, hydrobromide, hydrochloride, hydroxynapthoate, iodide, isothionate, lactate, lactobionate, malate, maleate, mandelate, mesylate, methylbromide, methylnitrate, methylsulfate, mucate, napsylate, nitrate, pamoate, pantothenate, phosphate, polygalactoronate, salicylate, stearate, subacetate, succinate, sulfate, tartrate, teoclate, triethiodide. The preferable salt used in this invention is granisetron hydrochloride, which is formed between granisetron and hydrochloric acid with a molar ratio of 1:1.

The dose of granisetron or a pharmaceutically salt thereof in this invention ranges between 0.01 mg and 30 mg, more preferably 0.05-10 mg, and most preferably 0.5-5 mg.

The composition may be in the forms of solution (aqueous or non-aqueous), or powder. The preferred form is aqueous solution due to the rapid drug release as well as minimal nasal irritation. The aqueous solution contains granisetron or a pharmaceutically salt thereof at a concentration from 0.1 to 300 mg/ml, more preferably from 0.5 to 100 mg/ml, most preferably from 1 to 50 mg/ml. A spray volume of the solution ranges from 10 to 200 µL, more preferably from 20 to 150 µL, and most preferably from 50 to 120 µL for each nostril.

One important aspect of the present invention is that the intranasal absorption of granisetron or a pharmaceutically salt thereof can further be enhanced by certain aqueous soluble polymers with bioadhesive properties, which effectively reduce mucocilliary clearance (MCC) and thus resulting in prolonged drug residence time intranasally as well as improved rate and extent of drug absorption. Preferably, granisetron hydrochloride is mixed with polymeric materials with bioadhesive properties, i.e. the bioadhesive polymers, which are selected from acacia, albumins, carboxymethylcellulose sodium, carrageenan, cellulose microcrystalline, cellulose acetate, chitosan, dextrin, gelatin, guar gum, hyaluronic acid, hydroxylethylcellulose, hydroxypropyl starch, hydroxypropylcellulose, hydroxymethylpropylcelloluse, methyl cellulose, polyethylene glycols, poly(m-ethyl vinyl ether/maleic anhydride), povidone, rafinose, shellac, sodium alginate, sodium starch glycolate, starch and pregelatinized starch, tragacanth, xanthan gum.

At present, nasal stinging sensation caused by granisetron and/or excipients has not been adequately controlled by the compositions disclosed in all existing patents known to the inventors. Surprisingly, it was found in the present invention that it is possible to minimize the stinging sensation by adding the aqueous vehicle polymers which are capable of instantly changing the rheological behavior in relation to ion, pH and temperature. These polymers keep low viscosity when the drug solution is stored in the container, therefore the drug solution can be easily and accurately applied using the common nasal spray devices. After delivered into nasal cavity, however, the solution viscosity will quickly and dramatically increase due to the phase transition triggered by the ions in nasal fluids, or by the pH or temperature change in nasal cavity, yielding a viscous gel which ensures a better and longer contact with the nasal mucosa. Absorption of granisetron or a pharmaceutically salt thereof through nasal mucosa is then enhanced and the pharmacological effect is prolonged accordingly. At the same time, the nasal stinging sensation is minimized by the controlled (i.e., slow and sustained) release of granisetron or a pharmaceutically salt thereof to nasal mucosa. Polymers applied to prepare the instant gel formulations include but not limited to carbomer, carrageenan, cellulose acetate phthalate (CAP), gellan gum, pectin, sodium alginate, and poloxamer. Although this provides surprisingly good results for Graniestron, once this results are known, a person of ordinary skill in the art may, according to the teaching of the present disclosure, find some other polymers that also provide satisfactory results in practicing the present invention.

In most situations, pharmaceutically acceptable buffering agents may be used to maintain the optimal pH conditions for achieving physicochemical stability and minimizing local irritation to nasal mucosa. The suitable pH range according to the present invention ranges from 3.0 to 9.0, preferably 4.0 to 7.0. The preferred buffering systems include without limitation to acetic buffer, boric buffer, citrate buffer, phosphate buffer, tartaric buffer, and tris buffer.

The present compositions also contain one of the pharmaceutical preservatives to maintain the microbiological stability. Suitable preservatives include benzalkonium chloride, benzethonium chloride, benzyl alcohol, chlorobutanol, chlorhexidine, methylparaben and propylparaben, phenylethyl alcohol, phenylmercuric acetate, thimerosal. The preferred preservatives without adverse effect on cillia include but not limited to benzyl alcohol, benzalconium chloride, chlorhexidine, and thimerosal.

Finally, the compositions of the present invention may also contain: (1) chelators, i.e. sodium EDTA; (2) antioxidant, i.e. sodium metabisulphite; (3) tonicity agents, including dextrose, glycerin, hydroxypropyl betadex, mannitol, sorbitol, potassium chloride, and sodium chloride; (4) absorption enhancers including but not limited to bile salts, cyclodextrins, fatty acids, fusidic acid derivatives, phosphatidylcholines, Laureth-9, oleic acid, surfactants, etc. (see Davis S S, Ilium L. Clin Pharmacokinet 2003. 42(13):1107-1128).

The granisetron or a pharmaceutically salt thereof compositions, preferably in solution form, should be sprayed into nasal cavity using a non-pressurized disperser. Suitable dispenser includes a spray pump and a bottle, and can deliver a single dose or multiple doses by mechanical actuation. A spray volume ranges from 10 to 200 µL, more preferably from 50 to 150 µL, and most preferably from 80 to 120 µL in each nostril.

Compositions of the present invention are administrated intranasally to a patient, for rapid and sustained prevention or relief of nausea and vomiting induced by cytotoxic chemotherapy, radiation, or surgery.

The following examples of formulations for intranasal administration of granisetron or a pharmaceutically salt thereof serve to illustrate the invention without limiting its scope.

EXAMPLE 1

Ion-Sensitive Composition of Granisetron

This example provides a description of the method for preparing the ion-sensitive composition for intranasal administration in accordance with the invention, which serves to illustrate the present invention without limiting its scope. Briefly, 5 g Gellan Gum was added to deionized water and dissolved by heating to 95° C. with moderate stirring. The solution was then cooled to below 40° C. and 5 mL benzyl alcohol was added under stirring. 5.59 g Granisetron Hydrochloride (equivalent to 5 g/L of granisetron free base) was then added and completely dissolved to obtain a clear solution. The osmolality of solution was adjusted to 280-350 mOsm/kg by Mannitol. The pH of solution was adjusted to 6.95 by 10 mg/ml L-Arginine solution. The solution was then filled into a spray nasal dispenser with and the applicator delivering a quantity comprising 0.5 mg granisetron per actuation (0.1 ml).

EXAMPLE 2

Temperature-Sensitive Composition of Granisetron

This example provides a description for making temperature-sensitive composition for nasal administration in accordance with the invention, which serves to illustrate the present invention without limiting its scope. 5.59 g Granisetron Hydrochloride, 60 g NaCL and 0.125 g Benzalconium Chloride was added in a stainless steel equipped with mixer, 0.8 L 0.05N HCL was then introduced under consistent stirring at the room temperature until a clear solution obtained. 175 g Poloxamer 188 was charged into the above solution and stir, after dissolve completely, 12 g Poloxamer 407 was added into the solution and stir for 5 minutes, and then the rest HCL solution was added to the metered amount (1 L). The solution was filled into a spray nasal dispenser with and the applicator delivering a quantity comprising 0.5 mg granisetron per actuation (0.1 ml).

EXAMPLE 3 pH-Sensitive Composition of Granisetron

This example provides a description for making pH-sensitive composition for nasal administration in accordance with the invention, which serves to illustrate the present invention without limiting its scope. 5.59 g Granisetron Hydrochloride and 0.125 g Benzalconium Chloride were charged in a stainless steel equipped with mixer, about 0.8 L purified water was then introduced and kept stirring at the room temperature until obtaining a clear solution. Solution pH was adjusted to 3.0 by HCL. 9 g Carbopol 934, was added into the above solution under stirring. The solution was then placed at 4° C. for 12 hr until a clear solution is obtained. The pH of solution was further adjusted to 4.0 by NaOH. Purified Water was added to the required volume (1 L). The solution was filled into a spray nasal dispenser with and the applicator delivering a quantity comprising 0.5 mg granisetron per actuation (0.1 ml).

EXAMPLE 4

Bioadhesive Composition of Granisetron

This example provides a description for making a bioadhesive composition without phase-transition property for nasal administration in accordance with the invention, which serves to illustrate the present invention without limiting its scope. 5.59 g Granisetron Hydrochloride, 8.9 g $Na_2HPO_4.2H_2O$, 1.86 g Citric Acid Anhydrous, 0.2 g EDTA.2Na and 0.125 g Benzalkonium Chloride were charged in a stainless steel equipped with mixer, about 0.8 L purified water was then introduced and keep stirring at the room temperature until obtaining a clear solution. 2.5 g Hypromellose (Methocel k100m Premium) was added into 25 ml hot distilled water (80-90° C.) with agitation until the powder is homogeneously dispersed. Hypromellose solution was then mixed with the drug solution under stirring until a clear solution obtained. Solution pH was adjusted to 6-7 by HCL or NaOH. Purified Water was added to the required volume (1 L). The solution was filtrated through 0.22-micron filter, and then filled into a spray nasal dispenser with and the applicator delivering a quantity comprising 0.5 mg granisetron per actuation (0.1 ml).

EXAMPLE 5

In Vitro Release of Ion-Sensitive Composition

In vitro release study of the Ion-Sensitive Composition described in EXAMPLE 1 were performed using Franz diffusion cell system consisted a vertical Franz-type glass diffusion cells (Hanson Research Corp., USA) with a magnetic stirrer (2mag Magnetic® motion, Munchen, Germany) and a thermostatic circulating water bath (PolyScience inc., Warrington, Pa., USA). The effective area of diffusion was 1.13 $cm^2$, and the receiver cell volume was 7 ml. The receiver cell was filled with simulated nasal electrolyte solution (SNES, containing 1.29 mg/ml KCl, 7.45 mg/ml NaCl and 0.32 mg/ml $CaCl_2.H_2O$) as diffusion medium at 32±0.5° C., stirred at 100 rpm. The semi-permeable membrane (Spectra/Por® membrane, MWCO: 12000-14000 Da, Spectrum Laboratories Inc., CA, USA), immersed in SNES for 24 h prior to study, was mounted on the top of receiver compartment. 0.2 ml of the Ion-Sensitive Composition was then dropped onto the membrane. The donor cap was covered and clamped. Aliquots (0.3 ml) of the receiving phase were collected at proper time intervals at 0.25, 0.5, 0.75, 1, 1.5, 2, 3, 4, 6 h and replaced with an equal volume of pre-warmed fresh diffusion medium. All collected samples were stored at −30° C. until analysis. The drug concentration in receiving samples were then qualified by a validate HPLC-UV method.

The cumulative in vitro granisetron hydrochloride release is shown in FIG. 1. The cumulative release of granisetron hydrochloride gradually increased with time. The release profile of granisetron hydrochloride from the composition mixed with SNES fits the first-order kinetics.

EXAMPLE 6

Water-holding Capacity of Ion-Sensitive Composition

The Ion-Sensitive Composition described in EXAMPLE 1 was mixed with SNES with a ratio of 2:1 in test tube, and placed for 2 min. Then, about 0.4 g of formed gel was accurately weighted into centriprep filter device of ultrafiltration tube (size: 0.5 ml, MWCO: 30 kDa, Millipore, Mass., USA) (total weight $W_0$), followed by centrifugation at 300 rpm for 1, 5, 10, 20 and 30 min. The gel with centriprep filter device was reweighted ($W_t$) to determine the water-holding capacity of the gel: $W_t/W_0 \times 100\%$.

Figure 2:
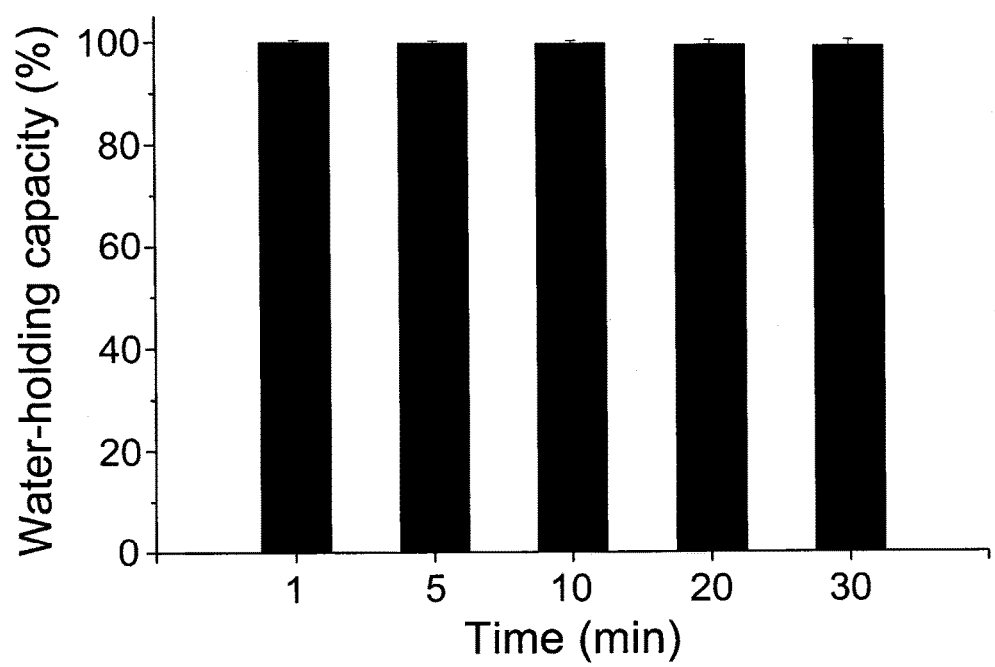
FIG. 2 shows the water-holding capacity of gellan gum based ion-sensitive composition at different centrifugation speed.

The water-holding capacity is generally expressed as the amount of water the gel structure can hold, or the capacity of the gel retain this water during storage or when subjected to external force. The ion-sensitive composition exhibited a water-holding capacity above 99% when subjected to a centrifugation (300 rpm) for 30 min (FIG. 2), suggesting that the in-situ gel has a stable structure of gel matrix, and not easy to be disturbed under low mechanic force.

EXAMPLE 7

Rheological Study of Ion-Sensitive Composition

The static rheological property of Ion-Sensitive Composition described in EXAMPLE 1 was investigated using rotational viscometer (Brookfield DV-II, Brookfield Engineering Laboratories Inc., MA, USA). Prior to measurement, the gel composition was mixed with SNES at different ratios (4:1, 2:1 and 1:1) and placed for 2 min. The mixture was then transferred into the small sample adapter of viscometer, and SC4-18 spindle was installed (the ratio of inner radius to outer radius was 0.92). Viscosity ($\eta$) was recorded as a function of increasing shear rate (y) from 3.96 to 132 $s^{-1}$. The rheological properties of the intact Ion-Sensitive Composition described in EXAMPLE 1 was also investigated and served as control. All the rheological measurements were performed in triplicate.

The viscosity of Ion-Sensitive Composition increased when mixed with SNES and the maximum viscosity was reached at the mixing ratio of 4:1. The viscosity decreased with the increase of shear rate, all tested samples demonstrated pseudoplastic fluid behavior. The viscosity at a shear rate of 3.96 $s^{-1}$ was summarized in Table 1. After mixed with SNES at 4:1, the formed gel has a ~10-fold higher viscosity, which facilitated to prolong the residence time of drug for its absorption in nasal cavity.

TABLE 1

Viscosity of Ion-Sensitive Composition in absence or presence of SNES

| Composition | Viscosity (Pa · s) |
| --- | --- |
| Ion-Sensitive Composition | 1.57 ± 0.21 |
| Ion-Sensitive Composition + SNES (4:1) | 2.53 ± 0.59 |
| Ion-Sensitive Composition + SNES (2:1) | 4.81 ± 1.02 |
| Ion-Sensitive Composition + SNES (1:1) | 17.48 ± 3.24 |

EXAMPLE 8

Spray Characterization of Bioadhesive Composition

Nasal sprays containing 3.5 mL Bioadhesive Compositions (granisetron concentration: 0.5% and 1.0%) were prepared according to the method described in EXAMPLE 4. The spray devices were automatically actuated by Mighty Runt Actuation Station, Innova System, Inc., USA. Spray pattern and plume geometry (spray angle) were tested by Spray View, Proveris Scientific Corp., USA; droplet size distribution were measured by Sympatec Helos/BF, Sympatec Gmbh, Germany; the fine droplet less than or equal to 9 μm was determined by Anderson Cascade Impactor, Copley Scientific, UK.

Results showed that the sprays are in the shape of ellipsoid with the ovality ratios ranging from 1.36 to 1.35 (Table 2). The spray angles are from 42-43° for both batches (Table 3). The droplets of both batches were narrowly distributed between 20 to 80 μm through the container life (Table 4), the fraction of fine droplets (aerodynamic diameter ≤9 μm) are less than 1%, indicating the minimal and negligible risk of lung deposition (Table 5).

TABLE 2

Spray pattern of Bioadhesive Composition

| Batch No. (Drug Conc.) | Distance (cm) | Spray Pattern (Mean, n = 3) |
| --- | --- | --- |
| GNS-B01-05 (0.5%) | 3 | Longest diameter: 37.8 mm<br>Shortest diameter: 28.0 mm<br>The ratio of longest diameter to shortest diameter: 1.360 |
| | 6 | The spray shape is too large, the camera can't collect |
| GNS-B01-10 (1.0%) | 3 | Longest diameter: 33.7 mm<br>Shortest diameter: 23.5 mm<br>The ratio of longest diameter to shortest diameter: 1.435 |
| | 6 | The spray shape is too large, the camera can't collect |

TABLE 3

Plume geometry (spray angle) of Bioadhesive Composition

| Batch No. (Drug Conc.) | Plume Geometry (Mean, n = 3) |
| --- | --- |
| GNS-B01-05 (0.5%) | 43.9° |
| GNS-B01-10 (1.0%) | 42.4° |

TABLE 4

Droplet size distribution of Bioadhesive Composition

| Batch No. (Conc.) | Distance (cm) | Phase | Droplet Size Distribution (μm) (Mean, n = 3) | | |
| --- | --- | --- | --- | --- | --- |
| | | | $D_{10}$ | $D_{50}$ | $D_{90}$ |
| GNS-B01-05 (0.5%) | 3 | Benign | 16.84 | 34.09 | 69.98 |
| | | End | 17.28 | 34.55 | 71.43 |
| | 6 | Benign | 24.02 | 41.31 | 70.02 |
| | | End | 22.80 | 40.95 | 68.09 |
| GNS-B01-10 (1.0%) | 3 | Benign | 18.49 | 37.53 | 82.06 |
| | | End | 17.84 | 37.17 | 80.43 |
| | 6 | Benign | 24.08 | 43.25 | 75.03 |
| | | End | 22.49 | 43.00 | 76.81 |

TABLE 5

Fine droplets of Bioadhesive Composition by Anderson Cascade Impactor

| Batch No. (Drug Conc.) | Droplet size less than or equal to 9 μm (Mean, n = 3) |
| --- | --- |
| GNS-B01-05 (0.5%) | 0.99% |
| GNS-B01-10 (1.0%) | 0.47% |

EXAMPLE 9

Pharmacokinetic Study on Ion-sensitive Composition in Rats

The study in this example was aimed at investigating the intranasal absorption of granisetron Ion-Sensitive Composition as compared to the drug solution formulation for intranasal and intravenous routes. SD rats (n=5-6 for each dose) received an intranasal dose (0.4 mg/kg) of solution composition (IN_solution) which was prepared according to the EXAMPLE 1 in CN Patent No. ZL021176716.8, an intranasal dose (0.4 mg/kg) of granisetron Ion-Sensitive Composition (IN-in situ gel) which was prepared according to the EXAMPLE 1 of this invention, and an intravenous dose (0.4 mg/kg) of granisetron solution (IV_solution) which was prepared by directly dissolving granisetron hydrochloride into saline solution to the final concentration of 0.33 mg/ml (free base). Multiple blood samples were collected from tail vein until 6 hrs. Granisetron concentration in rat plasma was determined using a validated HPLC-FLD method. The standard non-compartmental method was used to generate the pharmacokinetic parameters.

Figure 3:
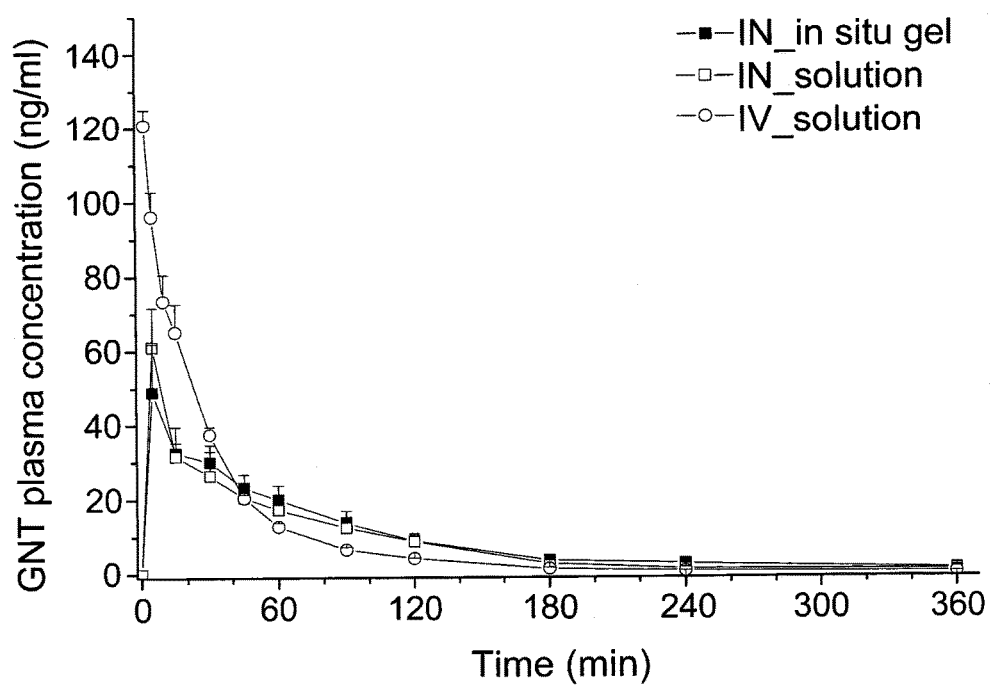
FIG. 3 shows the mean granisetron plasma concentration versus time profiles after intravenous administration of granisetron solution (IV_solution), an intranasal administration of ion-sensitive composition (IN_in situ gel) and a solution composition (IN_solution) at a single dose of 0.4 mg/kg in SD rats.

FIG. 3 shows the mean granisetron plasma concentration versus time profiles after intravenous administration of granisetron solution (IV_solution) and intranasal administration of Ion-Sensitive composition (IN_in situ gel), or solution composition (IN_solution) at a single dose of 0.4 mg/kg in rats. Results indicate the intranasal dose of Ion-Sensitive composition can achieve prolonged granisetron plasma concentration than the same intranasal dose of solution composition, especially during the first 3 hours.

The pharmacokinetic parameters for all formulations were summarized in the table below. Both granisetron Ion-Sensitive composition (IN_in situ gel) and solution composition (IN_solution) were rapidly absorbed after intranasal administration in rats.

TABLE 6

Pharmacokinetic parameters of granisetron after IV and IN administration of Granisetron formulations at a single dose of 0.4 mg/kg

| PK parameters | Nasal | | IV |
|---|---|---|---|
| | solution | in situ gel | solution |
| $T_{max}$ (min) | 5.0 ± 0.0 | 5.0 ± 0.0 | N.A. |
| $C_{max}$ (ng/ml) | 61.1 ± 10.6 | 48.9 ± 13.0 | 120.8 ± 4.3 |
| $AUC_{0-6\,h}$ (ng · min/ml) | 3053.4 ± 610.6 | 3364.6 ± 370.3 | 3405.0 ± 209.9 |
| $AUC_{0-\infty}$ (ng · min/ml) | 3134.7 ± 686.8 | 3499.2 ± 366.0 | 3429.2 ± 206.2 |
| $t_{1/2}$ (min) | 69.7 ± 25.7 | 81.5 ± 19.7 | 72.9 ± 10.9 |
| F (%) | 89.7 | 98.8 | N.A. |

N.A.: not applicable.
* p < 0.05.

EXAMPLE 10

Pharmacokinetic Study on Bioadhesive Composition in Rats

The study in this example was aimed at investigating the intranasal absorption of Granisetron Bioadhesive Composition (EXAMPLE 4) as compared to intranasal solution composition and marketed products for intravenous and oral routes. For intravenous administration (IV), 0.3 ml of 0.333 mg/ml test solution Kytril® IV Infusion (3 mg/3 ml) was given to short-term anesthetized rats via plastic tube (pre-cannulated in jugular vein the day before drug administration). For intranasal administration (IN), 20 µl of drug nasal formulation (10 µl for each nostril) was administrated to rats (5 mm depth into the nostril) by the aid of a micropipette. Rats were placed in supine position during intranasal administration. For oral administration, 1 ml of 0.1 mg/ml oral suspension formulation (prepared by dissolving 1 Kytril® tablet (1 mg) into 10 ml deionized water containing 0.5% CMCNa) was gavaged to rats. Multiple blood samples were collected from tail vein until 6 hrs. Granisetron concentration in rat plasma was determined using a validated HPLC-FLD method. The standard non-compartmental method was used to generate the pharmacokinetic parameters.

Figure 4:
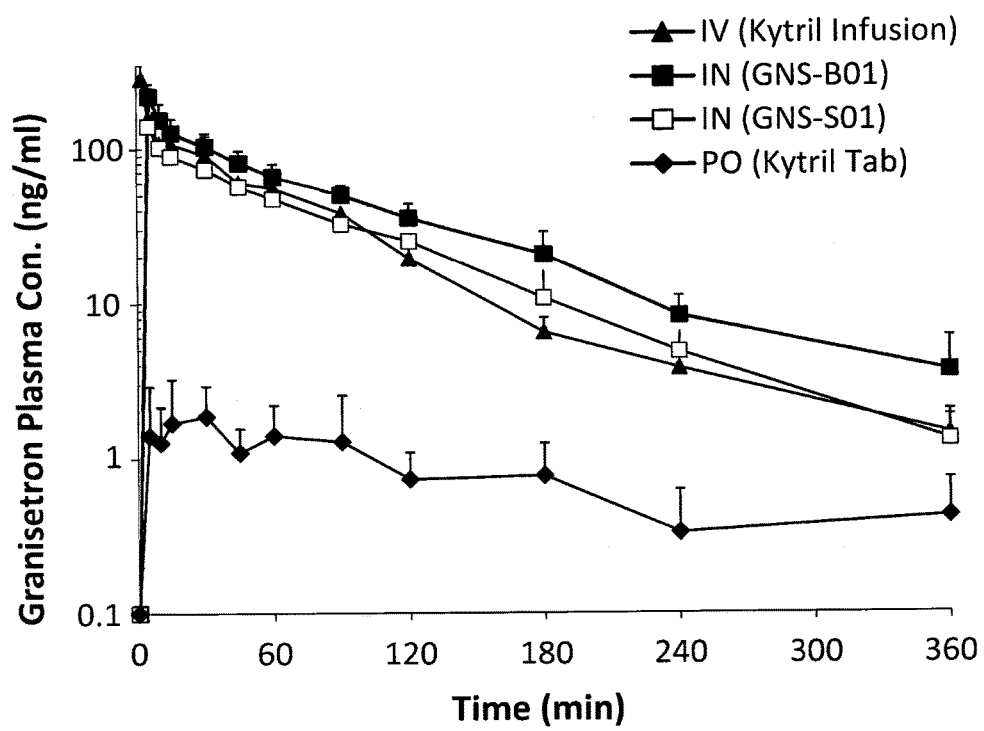
FIG. 4 shows the mean granisetron plasma concentration versus time profiles after intravenous administration of granisetron solution (Kytril® Infusion), oral administration of suspension prepared from Kytril® Tablet, and intranasal administration of bioadhesive composition (GNS-B01), or solution composition (GNS-S01) at a single dose of 0.4 mg/kg in SD rats.
Figure 5:
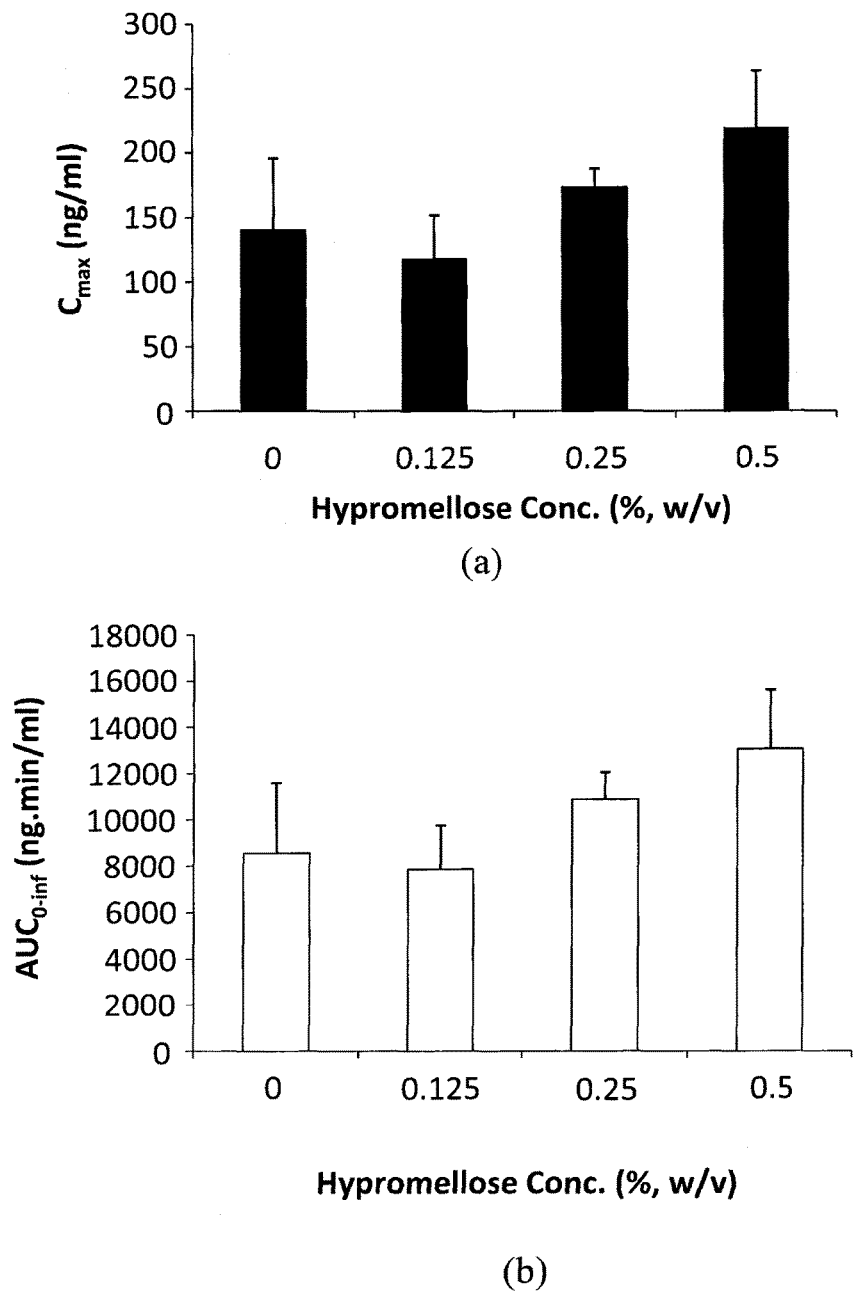
FIG. 5 shows (a) the mean peak plasma concentration ($C_{max}$) and (b) area under the curve ($AUC_{0-inf}$) after intranasal administration of granisetron bioadhesive compositions containing various percentage of Hypromellose in SD rats.

The mean plasma concentration-time profiles after intranasal, oral and intravenous administration of various compositions is shown in FIG. 4. The pharmacokinetic parameters are summarized in Table 7. Compared to the incomplete oral absorption of granisetron suspension prepared from tablets, the intranasal absorption of granisetron formulations were faster and complete, with significant earlier and higher drug plasma concentration which was comparable to intravenous administration. The elimination half-lives for all dose levels were around 1-1.5 hour for all routes of dosing. Following intranasal administration of granisetron bioadhesive formulations containing HPMC, $C_{max}$), and $AUC_{0-inf}$ increased with Hypromellose concentration (FIG. 5).

TABLE 7

Pharmacokinetic parameters of granisetron following intravenous, oral, and intranasal administration in rats

| | | Intravenous Kytril® | Oral Kytril® | Intranasal | |
|---|---|---|---|---|---|
| | | IV | Tab | GNS-S01 | GNS-B01 |
| PK Parameter | Statistics | 0.8 mg/kg (n = 5) | 0.8 mg/kg (n = 7) | 0.8 mg/kg (n = 6) | 0.8 mg/kg (n = 6) |
| $T_{max}$ (min) | Mean (SD) | — | 27.9 (29.0) | 5.0 (0.0) | 5.0 (0.0) |
| $C_{max}$ (ng/ml) | Mean (SD) | 290.2 (97.9) | 3.3 (1.3) | 140.4 (55.3) | 220.0 (44.7) |
| $AUC_{0-t}$ (ng · min/ml) | Mean (SD) | 9410.0 (2379.2) | 272.9 (42.6) | 8457.9 (3304.8) | 12741.8 (2464.8) |
| $AUC_{0-inf}$ (ng · min/ml) | Mean (SD) | 9801.1 (2450.5) | 315.2 (46.8) | 8555.9 (3036.1) | 13057.6 (2569.9) |
| $T_{1/2}$ (min) | Mean (SD) | 68.5 (13.4) | 94.9 (27.7) | 55.9 (5.4) | 65.3 (12.1) |
| F (%) | Mean | — | 3.2 | 87.3 | 133.2 |

EXAMPLE 11

Pharmacokinetic Study on Bioadhesive Composition in Beagle Dogs

This study is meant to evaluate the pharmacokinetic parameters of Granisetron intranasal spray compared to oral tablet and IV injection in Beagle dogs. Eight Beagle dogs (4 male and 4 female) participated in the study. The study was preceded in five cross-over periods, separated by 3-day washout period. For oral administration, dogs were fasted about 16 hours prior to the dosing but had free access to water. Dogs were orally administered 1 Kytril® tablet (1 mg) for the 1.0 mg/dog. Each oral dosing was administered with 20-30 mL of water. For intranasal administration, the spray device was primed 4-5 times prior to dose administration, dogs were allowed to stand or in an upright position, Granisetron bioadhesive composition was sprayed into the right nostril by pressing down the spray device evenly on both sides once. For IV administration, 1 mL Kytril® IV Infusion (3 mg/3 ml) was infused intravenously at the rate of 1 ml/min. Blood samples were collected at pre-dose (0 min) and at 5, 10, 15, 30, 45 minutes; and at 1, 2, 3, 4, 6, 8, 12, 24 hours post-dose. After the plasma-separation process, the samples were analyzed by a validated LC-MS/MS method.

Figure 6:
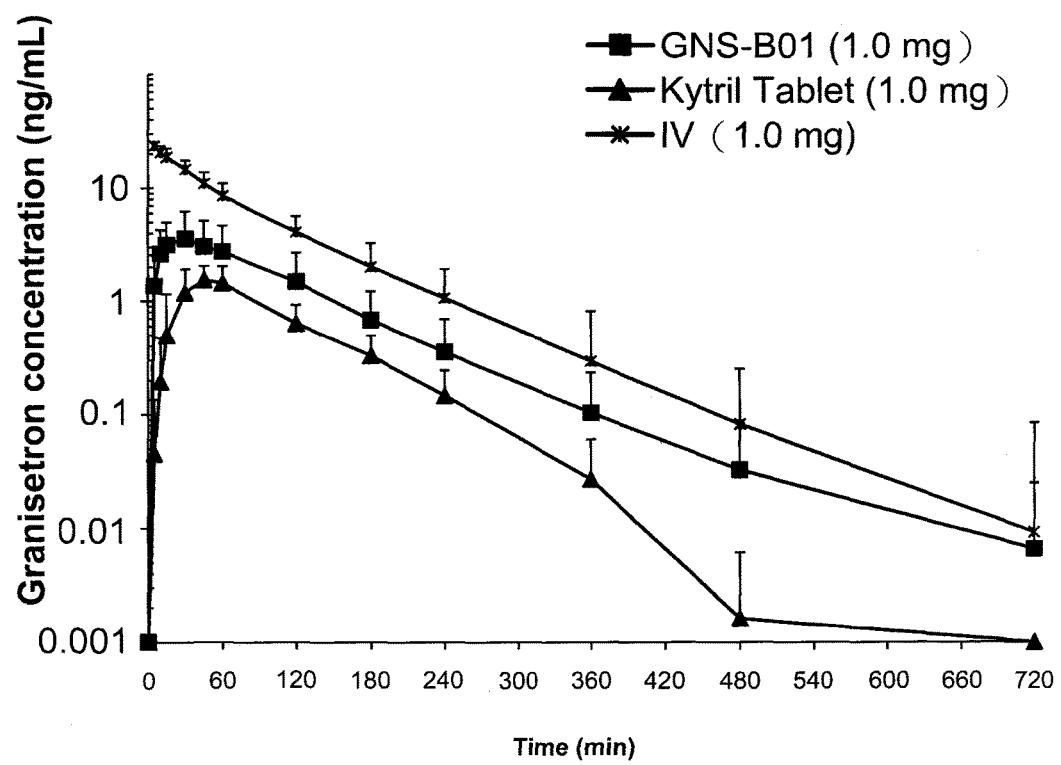
FIG. 6 shows the mean granisetron plasma concentration versus time profiles after intravenous administration of Kytril® Infusion (3 mg/3 mL), oral administration of Kytril® Tablet (1 mg), and intranasal administration of bioadhesive composition (GNS-B01) at a single dose of 1.0 mg in beagle dogs.
Figure 7:
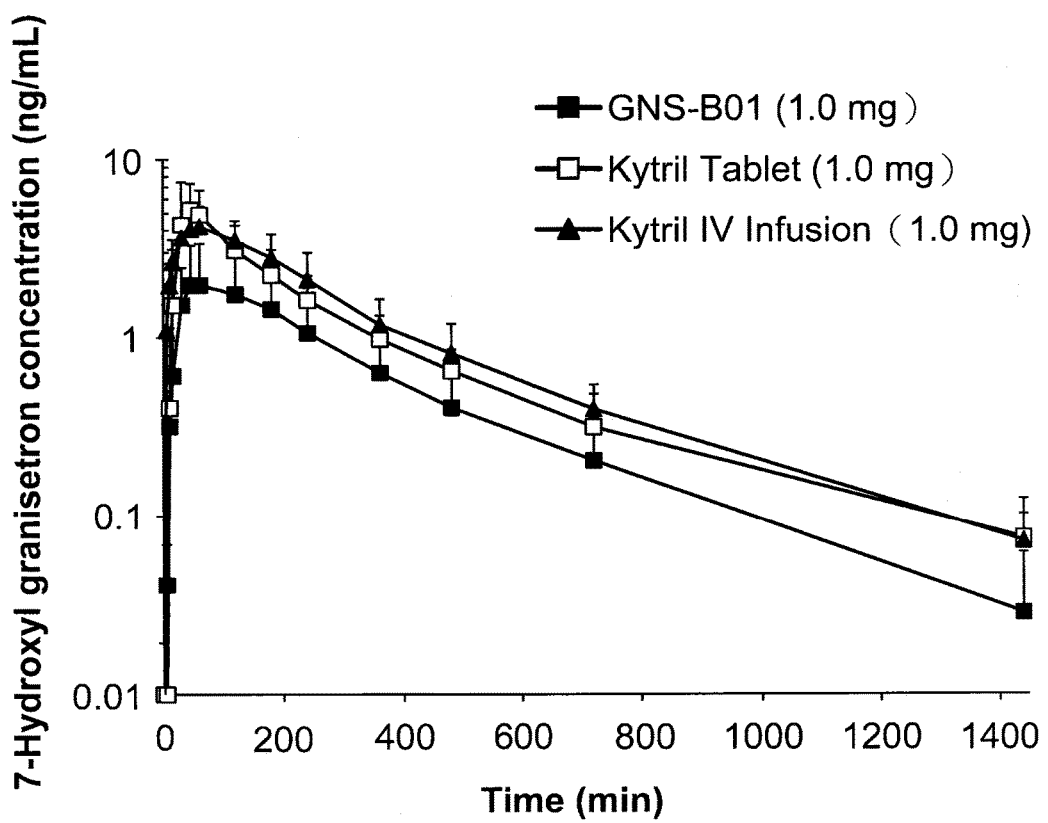
FIG. 7 shows the mean 7-hydroxyl granisetron plasma concentration versus time profiles after intravenous administration of Kytril® Infusion (3 mg/3 mL), oral administration of Kytril® Tablet (1 mg), and intranasal administration of bioadhesive composition (GNS-B01) at a single dose of 1.0 mg in beagle dogs.

The mean plasma concentration-time profiles after intranasal, oral and intravenous administration of various compositions is shown in FIG. 6. All dogs were exposed to the parent drug and all plasma samples were analyzed for Granisetron and its major metabolite 7-OH Granisetron. The mean 7-hydroxyl granisetron plasma concentration versus time profiles after intravenous administration of Kytril® Infusion (3 mg/3 mL), oral administration of Kytril® Tablet (1 mg), and intranasal administration of bioadhesive composition (GNS-B01) at a single dose of 1.0 mg in beagle dogs is shown in FIG. 7. The pharmacokinetic parameters of Granisetron and its major metabolite of 7-OH Granisetron are summarized in Tables 8 and 9.

At a dose of 1.0 mg/dog, the mean $T_{max}$ of Granisetron was 26.3 minutes (ranged 15.0-45.0) by intranasal administration compared to 43.1 minutes (ranged 30.0-60.0) by oral administration. This finding indicates that the absorption of Granisetron by the intranasal route was faster than that by oral dosing. The mean $C_{max}$ of 3.71 ng/mL and $AUC_{0-last}$ of 436 ng/mL*min by intranasal administration were at least twice as much as the mean $C_{max}$ of 1.78 ng/mL and $AUC_{0-last}$ of 177 ng/mL*min by oral administration. The terminal half-lives were similar for both dose administrations at about 60 minutes.

The major metabolite of 7-OH Granisetron was found in all dose levels. The amount of the 7-OH Granisetron was about twice as much as the plasma after oral dosing compared to intranasal administration.

TABLE 8

Mean pharmacokinetic parameters and absolute bioavailability of Granisetron in Beagle dogs

| | Analyte Granisetron Route | | | | |
|---|---|---|---|---|---|
| | Nasal Administration | | | Oral | IV |
| | Dosage (mg/dog) | | | | |
| PK Parameter | 0.5 Mean ± SD | 1.0 Mean ± SD | 2 Mean ± SD | 1 Mean ± SD | 1 Mean ± SD |
| $C_{max}$ (ng/mL) | 2.20 ± 1.48 | 3.71 ± 2.69 | 8.48 ± 4.21 | 1.78 ± 0.561 | 23.8 ± 3.16 |
| $T_{max}$ (min) | 26.9 ± 18.1 | 26.3 ± 10.6 | 23.8 ± 11.9 | 43.1 ± 12.5 | 5.63 ± 1.77 |
| $t_{1/2}$ (min) | 59.8 ± 14.7 | 63.9 ± 15.3 | 78.3 ± 21.1 | 58.6 ± 4.12 | 65.8 ± 10.7 |
| MRT (min) | 96.8 ± 33.2 | 86.9 ± 18.2 | 101 ± 17.0 | 90.1 ± 14.6 | 74.2 ± 12.1 |
| CL/F (L/min) | 4.20 ± 4.35 | 4.26 ± 3.69 | 2.80 ± 2.18 | 6.29 ± 2.68 | 0.61 ± 0.12 |
| Vz/F (L) | 348 ± 351 | 334 ± 217 | 286 ± 179 | 531 ± 234 | 56.9 ± 10.9 |
| $AUC_{0-last}$ (ng/mL*min) | 257 ± 210 | 436 ± 334 | 1001 ± 567 | 177 ± 73.7 | 1703 ± 386 |
| $AUC_{0-\infty}$ (ng/mL*min) | 264 ± 211 | 443 ± 334 | 1012 ± 571 | 184 ± 71.4 | 1714 ± 389 |
| Abs F (%) | 30.8 | 25.8 | 29.5 | 10.7 | — |

TABLE 9

Mean pharmacokinetic parameters of metabolite 7 OH-Granisetron in Beagle dogs

| | Analyte 7-OH Granisetron Route | | | | |
|---|---|---|---|---|---|
| | Nasal Administration | | | Oral | IV |
| | Dosage (mg) | | | | |
| PK Parameter | 0.5 Mean ± SD | 1.0 Mean ± SD | 2 Mean ± SD | 1 Mean ± SD | 1 Mean ± SD |
| $C_{max}$ (ng/mL) | 1.26 ± 0.845 | 2.18 ± 1.54 | 4.56 ± 2.01 | 5.73 ± 2.17 | 4.28 ± 1.20 |
| $T_{max}$ (min) | 60.0 ± 25.4 | 63.8 ± 23.7 | 65.6 ± 35.8 | 37.5 ± 16.0 | 48.8 ± 13.3 |
| $t_{1/2}$ (min) | 233 ± 72 | 262 ± 47 | 306 ± 33 | 275 ± 61 | 276 ± 0.2 |
| MRT (min) | 235 ± 49 | 265 ± 48 | 325 ± 21 | 270 ± 41 | 297 ± 19 |
| CL/F (L/min) | 2.98 ± 4.01 | 2.70 ± 2.36 | 1.50 ± 0.61 | 0.90 ± 0.32 | 0.77 ± 0.25 |
| Vz/F (L) | 1055 ± 1518 | 996 ± 871 | 672 ± 322 | 342 ± 102 | 317 ± 142 |
| $AUC_{0-last}$ (ng/mL*min) | 364 ± 263 | 664 ± 520 | 1549 ± 771 | 1197 ± 446 | 1389 ± 465 |
| $AUC_{0-\infty}$ (ng/mL*min) | 386 ± 264 | 691 ± 520 | 1609 ± 810 | 1246 ± 473 | 1419 ± 470 |

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodi-

EXAMPLE 12

Acute Toxicology and Toxicokinetic Study in Rats

A repeated dose 7-day intranasal instillation toxicity study in Sprague-Dawley rat was performed to evaluate the potential toxicity and toxicokinetics of Granisetron Nasal Spray.

Male and female rats were administered the vehicle solution or GNS at 0.2, 0.4, 0.8 mg/rat via daily intranasal instillation once daily for 7 consecutive days. The blood and urine were collected scheduled for clinical pathology. The animals were scheduled for necropsy on Study Day 8.

All the animals survived through the entire length of the study. There were no treatment-related gross or organ weight changes in the study animals examined. The only treatment-related finding was lymphoid hyperplasia in the tracheo-bronchial lymph node in GNS-treated males and females at 0.8 mg/animal.

Although there were no apparent fender differences in Cmax on D1 and D7, females had slightly higher AUCs than males. Increasing GNS level resulted in increases of Cmax and AUC0-24 h of D1 were not proportional to increase of GNS; those of D7 were fairly proportional. There were no apparent systemic accumulations by repeating daily dose for 7 consecutive days.

INDUSTRIAL APPLICABILITY

The method of the present invention can be applied to the field of preparation of pharmaceutical composition for intranasal administration.

What is claimed is:

1. An intranasal pharmaceutical composition, comprising (a) granisetron or a pharmaceutical salt, and (b) at least one aqueous vehicle polymer that is selected from the group consisting of a rheology-changeable polymer, a bioadhesive polymer, and a combination thereof,
   wherein said rheology-changeable polymer is selected from the group consisting of a pH-sensitive polymer, a temperature-sensitive polymer, an ion-sensitive polymer, and a combination thereof; said bioadhesive polymer is hypromellose; and said composition contains 1 to 50 mg/mL hypromellose.

2. The pharmaceutical composition of claim 1, wherein the rheology-changeable polymer is selected from the group consisting of carbomer, carrageenan, cellulose acetate phthalate, gellan gum, pectin, sodium alginate, poloxamer, and a combination thereof.

3. The pharmaceutical composition of claim 1, further comprising an aqueous solvent suitable for intranasal spray using a spray device.

4. The pharmaceutical composition of claim 1, wherein granisetron or a pharmaceutical salt is at a concentration of 0.5-100 mg/ml.

5. The pharmaceutical composition of claim 2, which has a pH from 3.0 to 9.0.

6. The pharmaceutical composition of claim 1, wherein said pH-Sensitive polymer is capable of changing the rheological behavior in relation to pH change.

7. The pharmaceutical composition of claim 6, wherein said pH-Sensitive polymer is carbomer.

8. The pharmaceutical composition of claim 7, wherein carbomer is at a concentration of 0.1 to 30 mg/ml.

9. The pharmaceutical composition of claim 6, wherein said pH-Sensitive polymer is cellulose acetate phthalate.

10. The pharmaceutical composition of claim 9, wherein cellulose acetate phthalate is at a concentration of 1 to 500 mg/ml.

11. The pharmaceutical composition of claim 1, wherein said Temperature-Sensitive polymer is capable of changing the rheological behavior in relation to temperature change.

12. The pharmaceutical composition of claim 11, wherein said Temperature-Sensitive polymer is poloxamer 407, poloxamer 188, or both.

13. The pharmaceutical composition of claim 12, wherein poloxamer 407 is at a concentration of 50 to 300 mg/ml, and poloxamer 188 is at a concentration of 5 to 50 mg/ml.

14. The pharmaceutical composition of claim 1, wherein said Ion-sensitive polymer is capable of changing the rheological behavior in presence of ions in nasal fluid.

15. The pharmaceutical composition of claim 14, wherein said Ion-sensitive polymer is gellan gum.

16. The pharmaceutical composition of claim 15, wherein gellan gum is at a concentration of 1 to 20 mg/ml.

17. The pharmaceutical composition of claim 14, wherein said Ion-sensitive polymer is pectin.

18. The pharmaceutical composition of claim 17, wherein pectin is at a concentration of 0.1 to 10 mg/ml.

19. The pharmaceutical composition of claim 1, comprising three aqueous vehicle polymers capable of changing the rheological behavior in relation to pH change, in relation to temperature change, and in presence of ions in nasal fluid, respectively.

20. The pharmaceutical composition of claim 1, further comprising an excipient, wherein said excipient comprises a bioadhesive polymeric material.

21. A method of prevention and/or relief of nausea and/or vomiting induced by cytotoxic chemotherapy, radiation, or surgery, comprising intranasally spraying an aqueous intranasal pharmaceutical composition of claim 1, which comprises granisetron or a pharmaceutical salt with a concentration of 0.5- 100 mg/ml of the active ingredient, wherein said composition is a solution containing 0.5- 100 mg/ml of the active ingredient and wherein said dose to generates a plasma concentration achieving therapeutic effects in 15 minutes, with the duration of no less than 3 hours.

* * * * *